United States Patent
Grbic et al.

(10) Patent No.: US 9,704,256 B2
(45) Date of Patent: Jul. 11, 2017

(54) SYSTEMS AND METHOD FOR COMPUTATION AND VISUALIZATION OF SEGMENTATION UNCERTAINTY IN MEDICAL IMAGES

(71) Applicant: Siemens Healthcare GmbH, Erlangen (DE)

(72) Inventors: Sasa Grbic, Princeton, NJ (US); Tommaso Mansi, Plainsboro, NJ (US); Ingmar Voigt, Erlangen (DE); Bogdan Georgescu, Plainsboro, NJ (US); Charles Henri Florin, Trenton, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 12 days.

(21) Appl. No.: 14/642,914

(22) Filed: Mar. 10, 2015

(65) Prior Publication Data
US 2016/0267673 A1  Sep. 15, 2016

(51) Int. Cl.
| | |
|---|---|
| G06T 7/62 | (2017.01) |
| G06T 7/00 | (2017.01) |
| G06F 19/00 | (2011.01) |
| G06T 19/00 | (2011.01) |
| G06T 7/11 | (2017.01) |
| G06T 7/174 | (2017.01) |

(52) U.S. Cl.
CPC .......... *G06T 7/0081* (2013.01); *G06F 19/321* (2013.01); *G06T 7/11* (2017.01); *G06T 7/174* (2017.01); *G06T 7/62* (2017.01); *G06T 19/00* (2013.01); *G06T 2200/04* (2013.01); *G06T 2207/10081* (2013.01); *G06T 2207/20081* (2013.01); *G06T 2207/30061* (2013.01); *G06T 2210/41* (2013.01)

(58) Field of Classification Search
CPC ....... G06T 19/00; G06T 2200/04; G06T 7/11; G06T 7/174; G06T 7/62
See application file for complete search history.

(56) References Cited

U.S. PATENT DOCUMENTS

| | | | |
|---|---|---|---|
| 8,698,801 B2 | 4/2014 | Vogt et al. | |
| 8,774,523 B2 | 7/2014 | Euler | |
| 2001/0042068 A1* | 11/2001 | Yoshida | ............... G05B 19/401 |
| 2011/0038516 A1 | 2/2011 | Koehler et al. | |
| 2013/0129174 A1* | 5/2013 | Grbic | .................... G06T 7/0012 |
| | | | 382/131 |

(Continued)

OTHER PUBLICATIONS

Y. Zheng, A. Barbu, B. Georgescu, M. Scheuering and D. Comaniciu, "Four-Chamber Heart Modeling and Automatic Segmentation for 3-D Cardiac CT Volumes Using Marginal Space Learning and Steerable Features," in IEEE Transactions on Medical Imaging, vol. 27, No. 11, pp. 1668-1681, Nov. 2008. doi: 10.1109/TMI.2008.2004421.*

(Continued)

*Primary Examiner* — Siamak Harandi (57) ABSTRACT

Systems and methods for computing uncertainty include generating a surface model of a target anatomical object from medical imaging data of a patient. Uncertainty is estimated at each of a plurality of vertices of the surface model. The uncertainty estimated at each of the plurality of vertices is visualized on the surface model.

29 Claims, 7 Drawing Sheets

(56) References Cited

U.S. PATENT DOCUMENTS

2014/0249784 A1    9/2014    Sankaran et al.

OTHER PUBLICATIONS

David B. Ress, Mark L. Harlow, Robert M. Marshall, Uel J. McMahan, Methods for Generating High-Resolution Structural Models from Electron Microscope Tomography Data, Structure, vol. 12, Issue 10, Oct. 2004, pp. 1763-1774, ISSN 0969-2126, http://dx.doi.org/10.1016/j.str.2004.07.022.*

* cited by examiner

SYSTEMS AND METHOD FOR COMPUTATION AND VISUALIZATION OF SEGMENTATION UNCERTAINTY IN MEDICAL IMAGES

BACKGROUND OF THE INVENTION

The present invention relates generally to uncertainty in medical images and more particularly to computation and visualization of segmentation uncertainty in medical images.

Many clinical applications nowadays rely on geometrical models for quantification of physiology and function. In a standard setting, these models are generated from two-dimension (2D), three-dimensional (3D), and 3D plus time (3D+t) medical images. Based on the estimated models, clinically relevant measurements are computed and used for diagnosis and intervention planning. For example, during transcatheter aortic valve implantation (TAVI) planning, a 3D computed tomography (CT) or transesophageal echocardiogram (TEE) image is acquired. Based on the 3D image, a patient specific surface model of the aortic valve can be extracted and distance measurements for implant sizing are derived. However, due to image noise and ill-defined boundaries caused by neighboring tissues with a similar imaging response, parts of the model boundary can be noisy, blurry, or have signal dropout. It is often challenging to correctly delineate the boundary of the anatomy in these situations. Thus, measurements derived solely from the geometric model inherit from the uncertainty of the model itself, yielding potentially sub-optimal diagnosis and planning data. In the example of TAVI, if the image at the aortic valve annulus is blurry or has signal dropout, the sizing of the implant might be sub-optimal if only the surface model is used.

BRIEF SUMMARY OF THE INVENTION

In accordance with an embodiment, systems and methods for computing uncertainty include generating a surface model of a target anatomical object from medical imaging data of a patient. Uncertainty is estimated at each of a plurality of vertices of the surface model. The uncertainty estimated at each of the plurality of vertices is visualized on the surface model.

In one embodiment, estimating uncertainty at each of the plurality of vertices of the surface model includes estimating a range of points along a surface normal for each of the plurality of vertices, and fitting an uncertainty distribution to the range of points estimated for each of the plurality of vertices. The range of points may correspond to a probability distribution indicating a probability that each point in the range of points accurately identifies an image boundary. Estimating the range of points along the surface normal for each of the plurality of vertices may include at least one of using a trained classifier to detect the range of points, and defining the range of points. The uncertainty distribution may be a Gaussian distribution.

In one embodiment, the uncertainty is refined by defining a minimum and a maximum for the range of points for at least one of the plurality of vertices.

In one embodiment, generating the surface model of the target anatomical object includes segmenting the target anatomical object using marginal space learning based segmentation. Segmenting the target anatomical object using marginal space learning based segmentation may include detecting a bounding box encapsulating the target anatomical object in the medical imaging data using marginal space learning, detecting anatomical landmarks of the target anatomical object within the bounding box, and fitting a surface model of the target anatomical object to the detected anatomical landmarks.

In one embodiment, visualizing the uncertainty estimated at each of the plurality of vertices on the surface model may include representing a level of uncertainty based on a color for each of the plurality of vertices, wherein the level of uncertainty is based on a standard deviation of the uncertainty distribution.

In one embodiment, a measurement of the patient is calculated based on the surface model and the uncertainty. The measurement may be represented as at least one of a range of the measurement based on the surface model and the uncertainty, and a mean value and a standard deviation value with an associated confidence interval.

These and other advantages of the invention will be apparent to those of ordinary skill in the art by reference to the following detailed description and the accompanying drawings.

DETAILED DESCRIPTION

The present invention generally relates to computation and visualization of segmentation uncertainty in medical images. Embodiments of the present invention are described herein to give a visual understanding of methods for computing and visualizing segmentation uncertainty in medical images. A digital image is often composed of digital representations of one or more objects (or shapes). The digital representation of an object is often described herein in terms of identifying and manipulating the objects. Such manipulations are virtual manipulations accomplished in the memory or other circuitry / hardware of a computer system. Accordingly, is to be understood that embodiments of the present invention may be performed within a computer system using data stored within the computer system.

Figure 1:
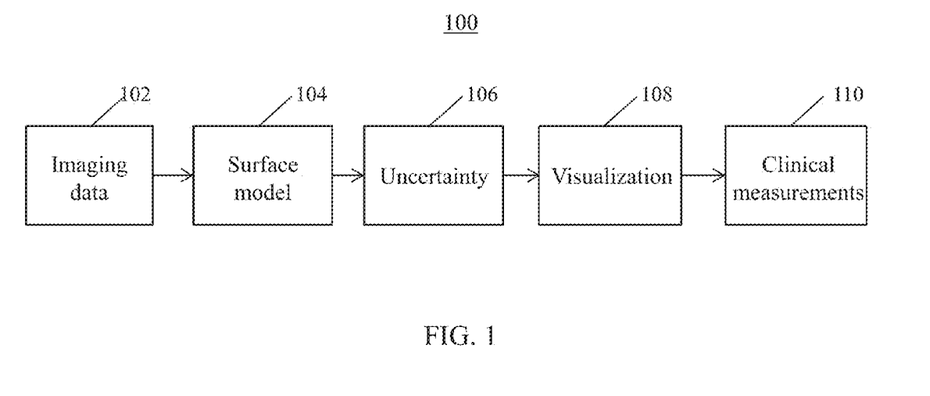
FIG. 1 shows a high-level framework for computing segmentation uncertainty, in accordance with one embodiment.

FIG. 1 shows a high-level framework 100 for computing segmentation uncertainty, in accordance with one or more embodiments. Framework 100 generates a surface model of an anatomical area of interest of a patient with an associated uncertainty using medical imaging data. It should be understood that while the embodiments discussed herein may be discussed for computing uncertainty in medical imaging data, the present principles are not so limited. Embodiments of the present invention may be employed to compute uncertainty for any imaging data.

Referring to FIG. 1, imaging data 102 of an area of interest of a subject (e.g., patient) are received. The imaging data may be from an imaging device of any modality, such as, e.g., computed tomography (CT), ultrasound (US), magnetic resonance imaging (MRI), etc. The area of interest may be a target anatomical object of the patient.

Surface model 104 of the target anatomical object is generated using imaging data 102. Surface model 104 may be a 3D surface model of the target anatomical object. Surface model 104 may be generated using any segmentation algorithm. In one embodiment, surface model 104 is generated using marginal space learning (MSL) based segmentation.

Uncertainty 106 is estimated on surface model 104. In one embodiment, uncertainty is estimated for each vertex of surface model 104 to calculate a range of acceptable boundary points using any machine learning based algorithm, such as, e.g., a probabilistic boosting tree classifier trained with image features. The range of acceptable boundary points corresponds to a probability distribution indicating a probability that each point in the range of acceptable boundary points accurate identifies an image boundary. Uncertainty 106 is quantified by fitting an uncertainty distribution (e.g., a Gaussian distribution) to the range of acceptable boundary points.

Visualization 108 is provided having uncertainty 106 overlaid on surface model 104. A level of uncertainty for each voxel may be visually represented on surface model 104. For example, in one embodiment, different colors may represent different levels of uncertainty.

Clinical measurements 110 of the target anatomical object may be calculated using surface model 104 and uncertainty 106. Clinical measurements 110 may include a diameter, area, distance, or any other measurement. For example, clinical measurements 110 may include a range of values based on uncertainty 106 rather than a single value.

Advantageously, framework 100 may be used for quantification, diagnosis, treatment planning, and interventional guidance. Framework 100 enables a user (e.g., physician) to visualize the uncertainty at each point of the surface model of anatomical target object of the patient.

Figure 2:
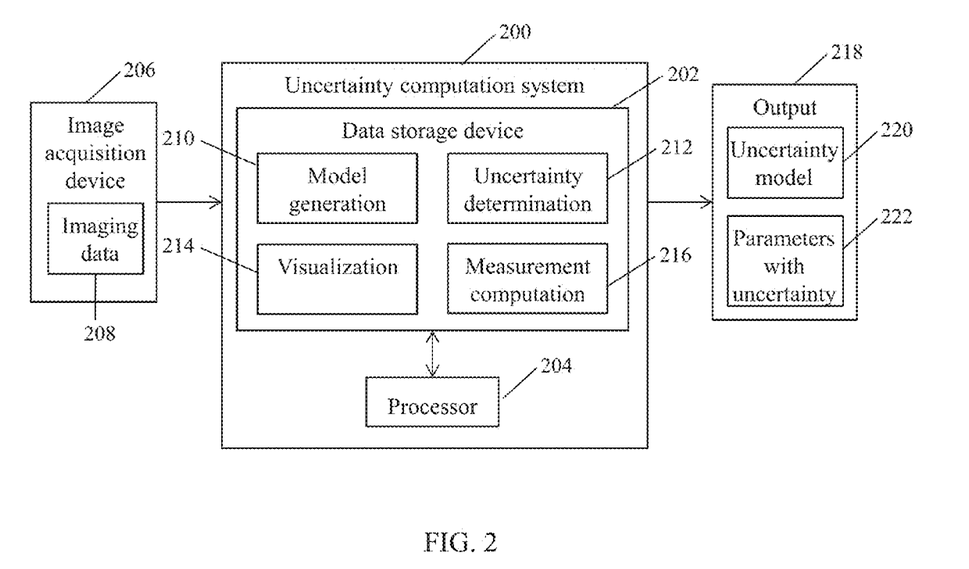
FIG. 2 shows a system for computing uncertainty in medical imaging data, in accordance with one embodiment.

FIG. 2 shows a detailed view of a system 200 for computing uncertainty in medical imaging data, in accordance with one or more embodiments. System 200 includes data storage device 202 interacting with one or more processors 204. It should be understood that system 200 may also include additional elements, such as, e.g., an input/output interface, a communications interface, etc.

System 200 receives imaging data 208 of a target object of a subject from image acquisition device 206 as input. Imaging data 208 is preferably medical imaging data of a target anatomical object of interest of a patient. Image acquisition device 206 may be of any imaging modality, such as, e.g., CT, US, MRI, etc. Imaging data 208 may include two-dimensional (2D) imaging data, 3D imaging data, 3D plus time (3D+t) imaging data, or any other suitable imaging data. In one embodiment, imaging data 208 is received by system 200 directly from image acquisition device 206 imaging the patient. In another embodiment, imaging data 208 is received by loading previously stored imaging data of the patient acquired using image acquisition device 206.

Model generation module 210 is configured to generate a surface model of the target anatomical object from imaging data 208. The generated surface model may be a 3D surface model. Model generation module 210 may apply any segmentation algorithm to generate the surface model. For example, a marginal space learning (MSL) based framework may be employed to generate the surface model. To efficiently handle the anatomical complexity, the surface model may be constructed hierarchically by detecting a bounding box encapsulating the target anatomical object in imaging data 208, identifying key anatomical landmarks on the target anatomical object, and fitting a full surface model including a detailed surface mesh to the anatomical landmarks to generate a patient specific surface model.

Figure 3:
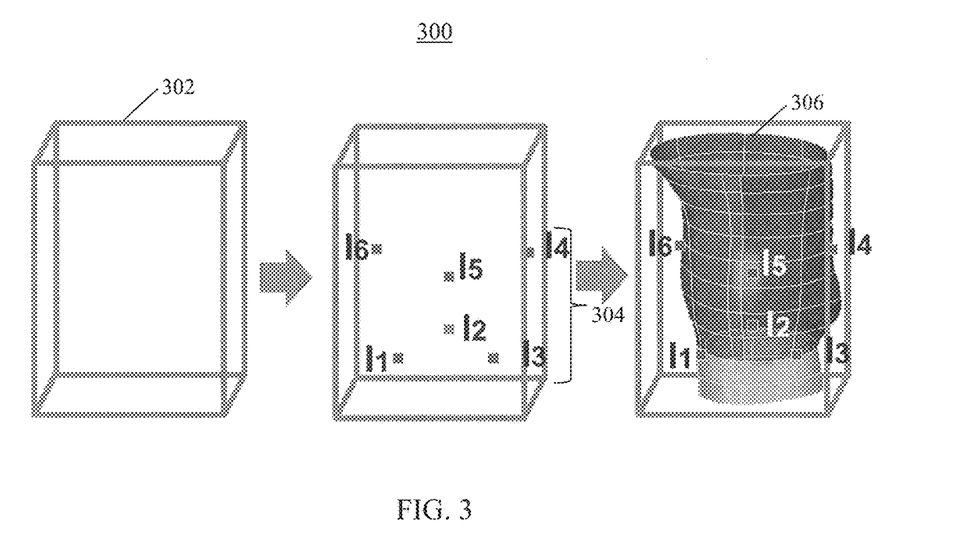
FIG. 3 shows an overview of the multiple space learning based framework for generating a surface model of a target anatomical object, in accordance with one embodiment.

FIG. 3 shows an overview of the MSL based framework for generating a surface model of a target anatomical object using machine learning based algorithms, in accordance with one or more embodiments. While the target anatomical object shown in FIG. 3 is an aortic valve, it should be understood that the target anatomical object may be any object of interest (e.g., liver, left ventricle, etc.).

Bounding box 302, which defines an initial pose of the aortic valve, is first detected from imaging data 208 using MSL based 3D object detection. MSL provides an efficient technique for learning high dimensional models and fast online searching by operating in subspaces of increasing dimensionality. Accordingly, the idea of MSL is to incrementally learn classifiers in the series of marginal spaces. As the dimensionality increases, the valid space region becomes more restricted by previous marginal space classifiers. The 3D object detection (global location estimation) is split into three steps: object position estimation, position-orientation estimation, and position-orientation-scale estimation. A separate classifier is trained based on annotated training data for each of these steps (e.g., in an offline step). Each classifier can be trained using a probabilistic boosting tree (PBT) in combination with Haar and/or steerable features based on a set of annotated training data. This results in the estimated affine transformation (position, orientation, and scale) defining a bounding box as a course representation of the global location of the aortic valve model in imaging data 208. It should be understood that any machine learning based algorithm may be employed, such as, e.g., deep learning methods.

Once bounding box 302 is detected in imaging data 208, anatomical landmarks 304 are detected from imaging data 208 within bounding box 302. Anatomical landmarks 304 are points on the aortic valve that have an anatomical meaning. For example, anatomical landmarks 304 may include aortic valve commissures, aortic valve hinges, aortic root, etc. Anatomical landmarks 304 include landmarks I1, . . . , I6, which are detected in imaging data 208 using respective trained landmark detectors. Anatomical landmarks 304 may include any number of anatomical landmarks, such as, e.g., 5 to 15 anatomical landmarks. An independent landmark detector is trained for each of the anatomical landmarks. In one embodiment, each landmark detector is trained as a PBT classifier using Haar features based on annotated training data. The trained landmark detectors search for the respective landmarks in the smaller subspace of bounding box 302 rather than the entire image space in imaging data 208. Thus, the landmark detection may be performed on a finer resolution than the global localization.

Surface model 306 of the aortic valve is fit to anatomical landmarks 304 to provide a patient specific surface model. Surface model 306 may comprise a detailed surface mesh representation of an aortic valve having any number of surface points. For example, surface model 306 may include, e.g., hundreds to thousands of surface points (not shows). Surface model 306 fit to anatomical landmarks 304 provides for a patient specific aortic valve model. Each anatomical landmark 205 and each surface point is a vertex on the patient specific aortic valve model.

In one embodiment, such MSL based framework may be employed using the method described in U.S. Pat. No. 8,934,693, entitled "Method and System for Intervention Planning for Transcatheter Aortic Valve Implantation from 3D Computed Tomography Data," which is incorporated herein by reference in its entirety.

Figure 4:
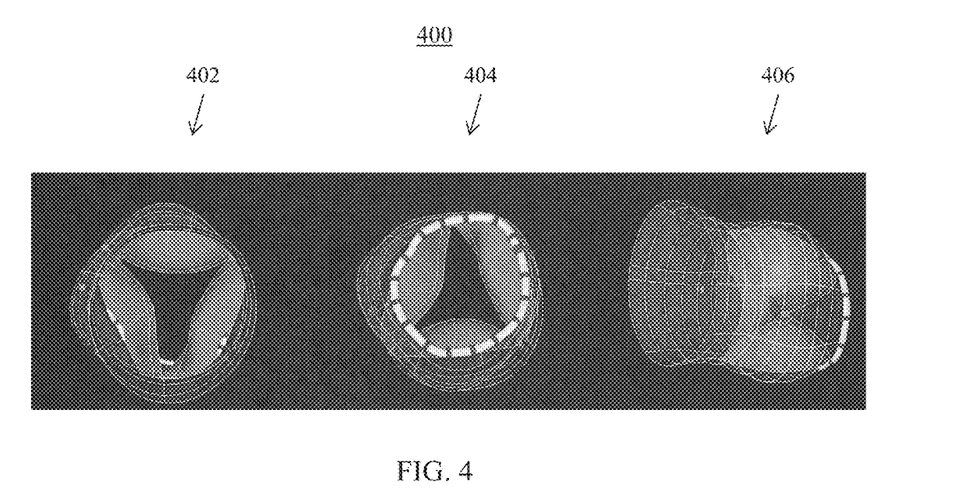
FIG. 4 illustrates an exemplary surface model of an aortic valve generated from imaging data, in accordance with one embodiment.

FIG. 4 illustrates an exemplary surface model 400 of an aortic valve generated from imaging data 208, in accordance with one or more embodiments. Surface model 400 of the aortic valve is shown with the aortic valve root and three leaflets. Surface model 400 of the aortic valve is generated from 3D CT imaging data. FIG. 4 includes top view 402, bottom view 404, and side view 406 of surface model 400 of the aortic valve.

Returning to FIG. 2, uncertainty determination module 212 is configured to estimate uncertainty at each vertex of the surface model to provide an uncertainty model. Uncertainty in the surface model may be due to, e.g., an image boundary being unclearly delineated or nonexistent (e.g., from signal dropout in transesophageal echocardiogram), or may be due to the image boundary having multiple responses in a certain range.

Uncertainty determination module 212 determines a range of acceptable boundary points along the surface normal for each vertex. In one embodiment, a classifier, such as, e.g., a PBT classifier, trained with image features extracted from a set of annotated training data, is employed to determine the range of acceptable boundary points for each vertex. Each vertex corresponds to a point on the boundary of the segmented surface. The trained classifier detects a probability for the points along a surface normal at each point. The range of acceptable boundary points is defined based on the probability values determined by classifier (e.g., as compared to a threshold). The range of acceptable boundary points may correspond to a probability distribution indicating a probability that each point in the range of acceptable boundary points accurately identifies an image boundary. In some embodiments, a user may define the range of acceptable boundary points.

Figure 5:
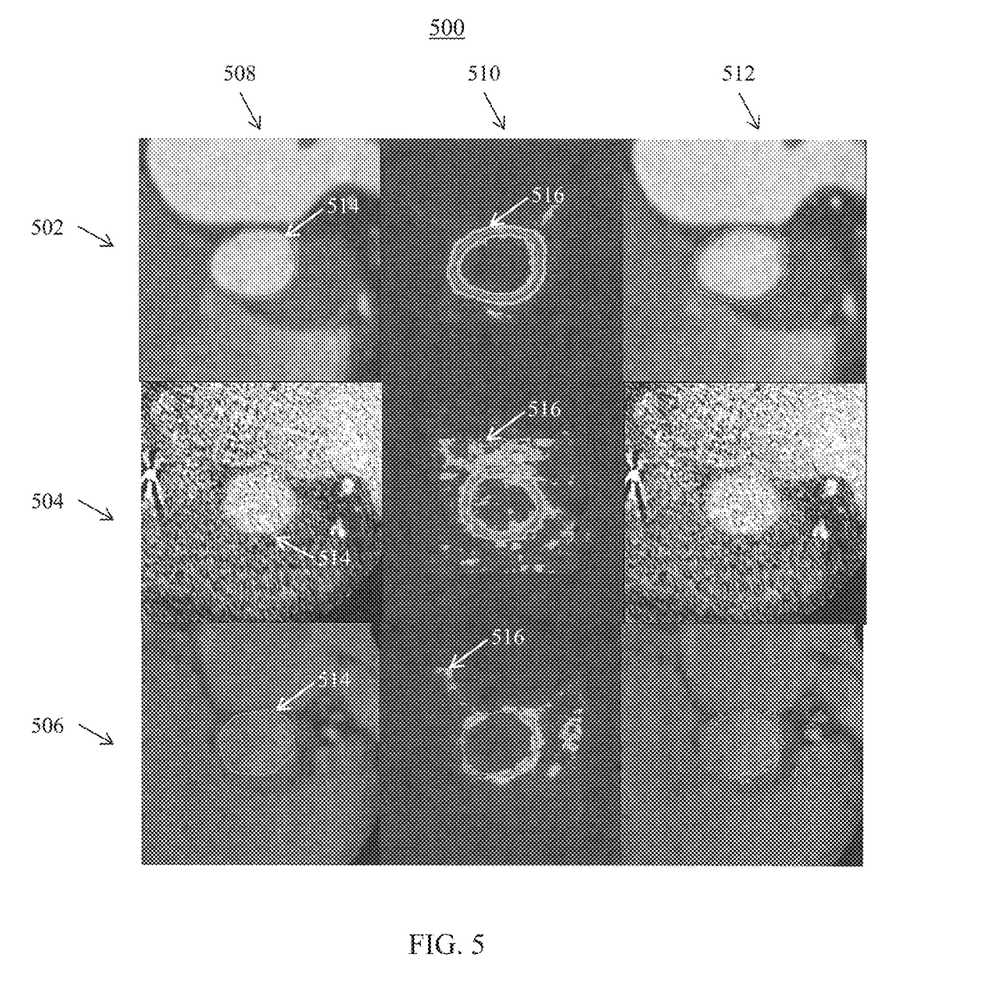
FIG. 5 illustrates exemplary visualizations of classifier output used to calculate uncertainty, in accordance with one embodiment.

FIG. 5 illustrates exemplary visualizations 500 of classifier output used to calculate uncertainty, in accordance with one or more embodiments. Visualizations 500 include examples 502, 504, and 506 of the aortic valve annulus. Column 508 shows CT images for the aortic valve annulus contour 514. Column 510 shows a probability map including highlighted portions 516 of the aortic valve boundary locations corresponding to the probability distribution (e.g., as output by the classifier). Column 512 shows a fused image of the probability map and the CT image.

Uncertainty determination module 212 quantifies the uncertainty by fitting a respective uncertainty distribution to the range of acceptable boundary points determined for each vertex. Specifically, the uncertainty distribution for each vertex is fit to the probability distribution associated with the range of acceptable boundary points for that vertex. In one embodiment, the uncertainty distribution may be a Gaussian distribution. Other distributions may also be employed.

Figure 6:
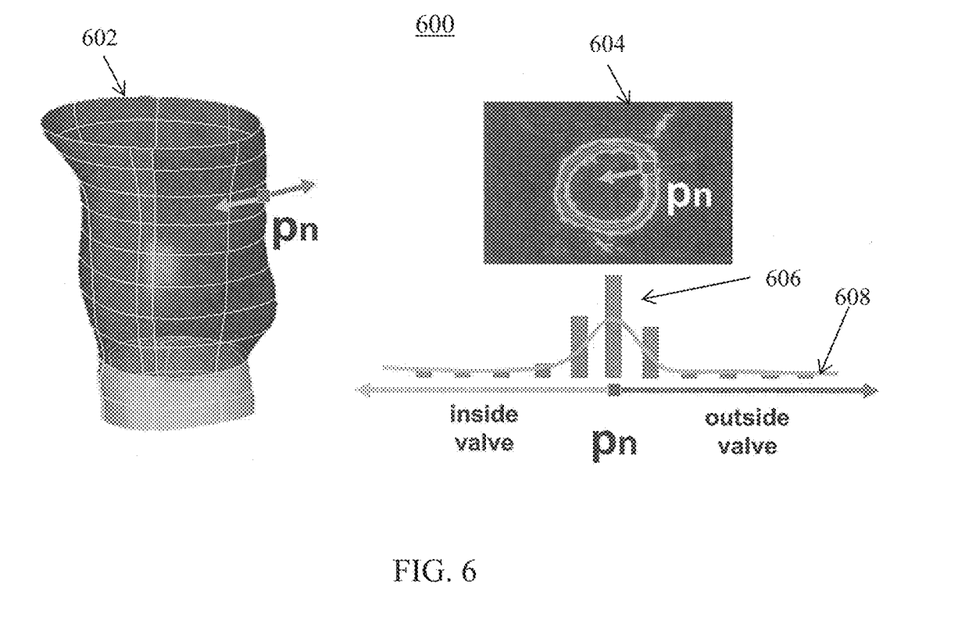
FIG. 6 shows an overview of quantifying uncertainty, in accordance with one embodiment.

FIG. 6 shows an overview 600 of quantifying uncertainty, in accordance with one or more embodiments. As discussed above, a classifier determines a probability distribution 606 corresponding to a range of points along the surface normal for a particular vertex $p_n$ of surface model 602 of the aortic valve. Probability distribution 606 corresponds to probabilities that each point in the range of points along the surface normal of vertex $p_n$ identifies an image boundary. As shown by the arrows extending from vertex $p_n$ in top down view 604 of surface model 602, the range of points along the surface normal of vertex $p_n$ may be inside the valve or outside the valve from vertex $p_n$. Gaussian distribution 608 is fit to probability distribution 606 of the range of acceptable boundary points for vertex $p_n$. The mean $\mu$ and standard deviation $\sigma$ can be extracted from Gaussian distribution 608. Thus, a value representing uncertainty for vertex $p_n$ can be computed as equation (1) below.

$$\text{uncertainty}(p_n, \mu, \sigma) = \frac{1}{\sigma\sqrt{2\pi}} e^{-\frac{(p_n-\mu)^2}{2\sigma^2}} \tag{1}$$

In one embodiment, a user can further refine the uncertainty model by defining a minimum and maximum for the range of acceptable boundary points along the surface normal for each vertex. A one-dimensional (1D) Gaussian distribution can be fit to the range of acceptable boundary points based on the defined minimum acceptable boundary point $p_{min}$ and maximum acceptable boundary point $p_{max}$ for each vertex. The mean of the Gaussian distribution is located at the boundary point (i.e., vertex) and the standard deviation defines a confidence interval. A value representing uncertainty in the surface model can be computed as in equation (2) below based on the user defined range of acceptable boundary points.

$$\text{uncertainty}(p_n, \mu, \sigma) = \frac{1}{\sigma\sqrt{2\pi}} e^{-\frac{(p_n-\mu)^2}{2\sigma^2}}, \tag{2}$$

$$p_n = \frac{p_{min} + p_{max}}{2}; \sigma = \frac{\|p_{max} - p_n\|}{2}$$

In one embodiment, the uncertainty model may be fed back to the segmentation algorithm for training the machine-learning based classifiers used for segmenting the object in the imaging data. For example, regions have a high certainty may be selected for training, while uncertain regions may not be selected as positives in discriminative learning pipeline.

Returning to FIG. 2, visualization module 214 is configured to generate a visualization of the uncertainty on the surface model. For example, uncertainty may be overlaid over the surface model for each vertex. Levels of uncertainty may be visually distinguished on the surface model for each vertex. The levels of uncertainty may be based on the standard deviation or variance of the Gaussian distribution. In one embodiment, uncertainty may be represented on the surface model using different colors corresponding to different levels of uncertainty. It should be understood that any other visual distinction may also be employed within the context of the present principles to represent levels of uncertainty.

Figure 7:
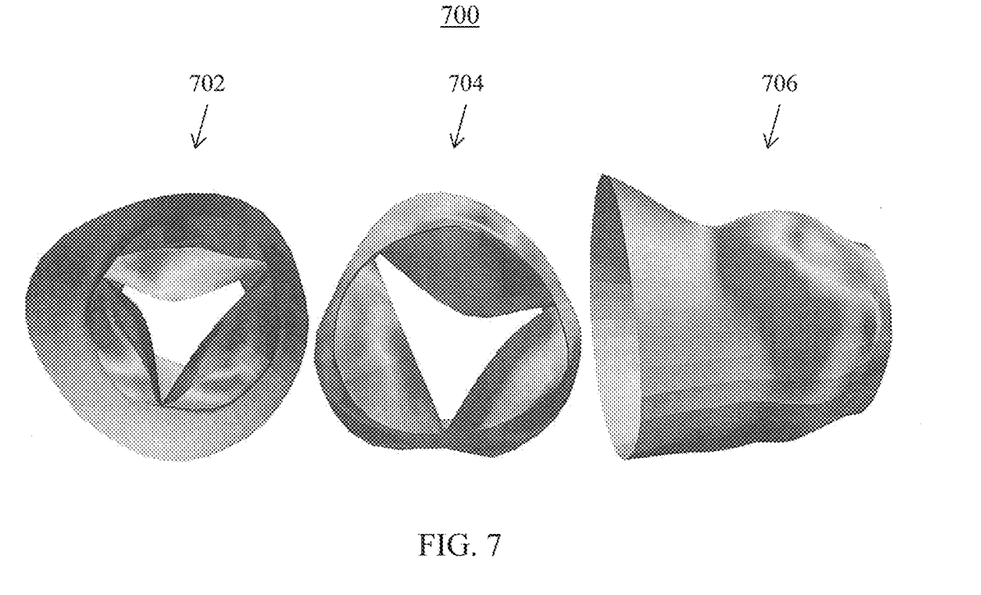
FIG. 7 illustrates an exemplary surface model with overlaid uncertainties, in accordance with one embodiment.

FIG. 7 illustrates an exemplary surface model 700 with overlaid uncertainties, in accordance with one or more embodiments. Surface model 700 includes top view 702, bottom view 704, and side view 706. Uncertainties are visually represented on surface model 700, e.g., by color or shading. For example, although surface model 700 in FIG. 7 is shown in black and white, surface model 700 can include designated colors or shadings representing different levels of boundary contour uncertainties. For example, surface model 700 can be visualized with red portions indicating high boundary contour uncertainty and blue portions indicating confidant boundary locations.

In one embodiment, visualization module 214 may animate the mesh along the uncertainty to enable visualization of possible segmentation solutions. For example, during an intervention, a user may select one model based on the additional information obtained during the intervention (e.g., contrast, new images, etc.), thus further reducing the uncertainty and improving the decision process.

Measurement computation module 216 is configured to calculate measurements of objects on the surface model based on the uncertainty. For example, a diameter, area, distance, or any other measurement of objects on the surface model may be computed taking into account the uncertainty. The parameter computed based on the uncertainty may be represented as a range of values. In some embodiments, the parameter may be represented as a mean value plus or minus the standard deviation and with a percent confidence interval.

In one embodiment, measurements of an object on the surface model are represented as a range of values between a minimum value and a maximum value based on the uncertainty. In other embodiments, measurements of an object on the surface model may be computed probabilistically. For example, a minimum and a maximum distance can be estimated for a given confidence interval (e.g., 95% confidence) based on the uncertainty. In another embodiment, stochastic methods may be applied where point configurations can be drawn based on the uncertainty surface model. Other approaches for computing parameters of objects on the surface model based on the uncertainty may also be employed.

Figure 8:
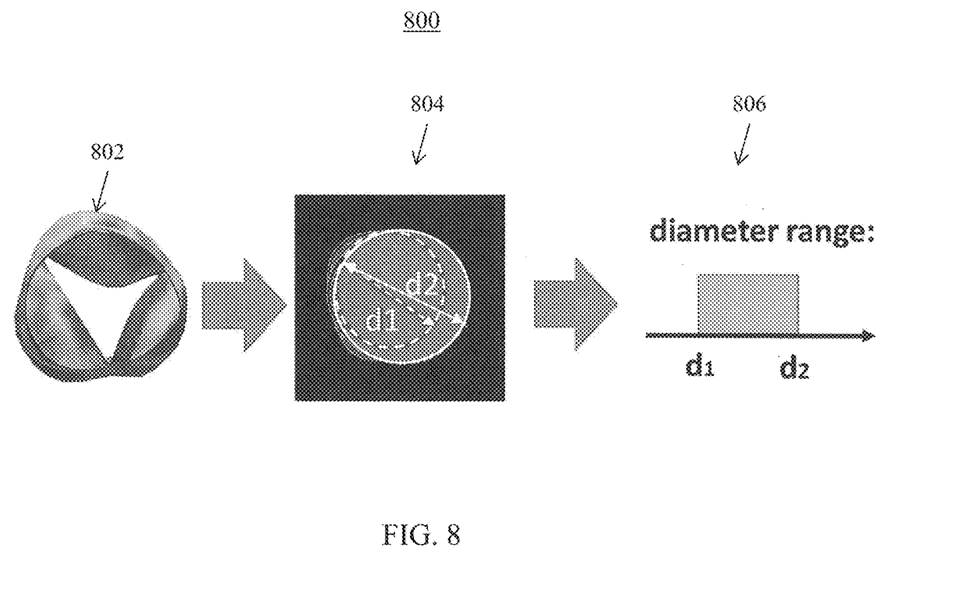
FIG. 8 illustrates an exemplary computation of the diameter of the aortic valve annulus based on uncertainty, in accordance with one embodiment.

FIG. 8 illustrates an exemplary computation 800 of the diameter of the aortic valve annulus based on uncertainty, in accordance with one or more embodiments. Uncertainty surface model 802 is used to calculate a diameter range for the aortic valve annulus. A minimum diameter d1 (shown as a dashed line in FIG. 8) and a maximum diameter d2 (shown as a solid line in FIG. 8) of the aortic valve annulus are estimated based on the uncertainty, shown in view 804. The diameter range 806 of the aortic valve is provided as a range of values from minimum diameter d1 to the maximum diameter d2 (e.g., 8 mm to 12 mm).

Advantageously, system 200 determines an uncertainty associated with each vertex of a surface model. Based on the estimated uncertainty, a user (e.g., physician) may alter the regular workflow for quantification and intervention planning. For example, in the case of implant sizing for TAVI, if uncertainty is less than 0.5 mm, the physician may proceed with the current measurement for sizing (as devices come in 3 mm ranges). However, if uncertainty is greater than 2 mm, the physician may decide to re-image the target anatomical object (e.g., using a different modality).

Figure 9:
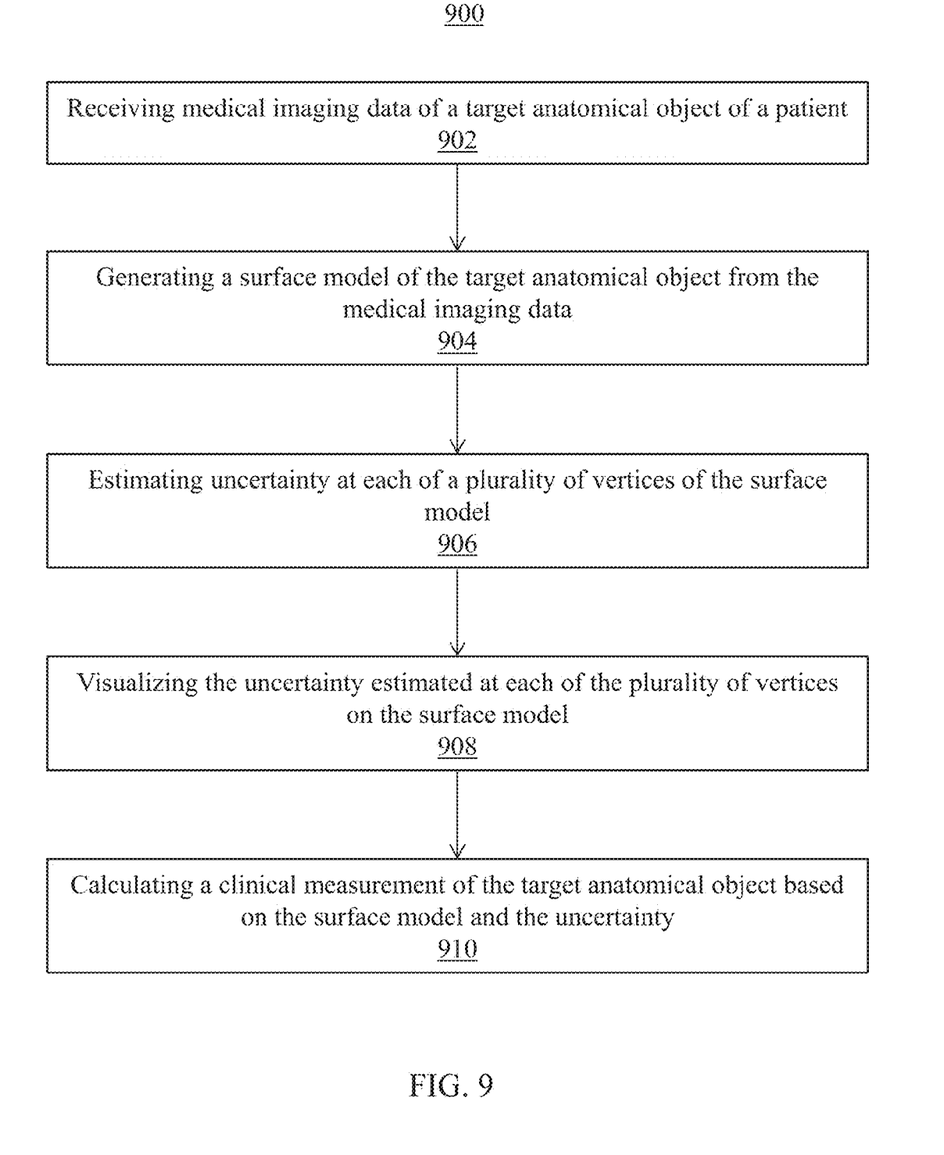
FIG. 9 shows a method for computing uncertainty in medical imaging data, in accordance with one embodiment.

FIG. 9 shows a method 900 for computing uncertainty in medical imaging data, in accordance with one or more embodiment. At step 902, medical imaging data of a target anatomical object of a patient is received. The medical imaging data may be of any modality, such as, e.g., CT, US, MRI, etc. The medical imaging data preferably include 3D imaging data, but may include any suitable imaging data. The medical imaging data may be received directly from an image acquisition device or may be received by loading previously stored medical imaging data.

At step 904, a surface model of the target anatomical object is generated from the medical imaging data. The surface model may be a 3D surface model of the target anatomical object. The surface model may be generated using any segmentation algorithm, such as, e.g., MSL based framework described above in connection with FIG. 3. For example, the surface model may be generated by first detecting a bounding box as a course representation of the target anatomical object using MSL and any trained machine learning based algorithm, such as, e.g., PBT. Anatomical landmarks of the target anatomical object may then be identified within the bounding box in the medical imaging data using trained landmark detectors. A surface model of the target anatomical object is then fit to the anatomical landmarks to provide a patient specific surface model. The surface model includes a surface mesh comprising surface points. The anatomical landmarks and surface points are vertices of the surface model.

At step 906, uncertainty is estimated at each of the plurality of vertices of the surface model. In one embodiment, a trained classifier (e.g., PBT classifier) determines a range of acceptable boundary points along the surface normal of each vertex. The range of acceptable boundary points may correspond to a probability distribution indicating a probability calculated by the trained classifier that each point of the range of acceptable boundary points accurately identifies an image boundary. The uncertainty is quantified by fitting a respective uncertainty distribution (e.g., Gaussian distribution) to the probability distribution of the range of acceptable boundary points determined for each vertex. In one embodiment, uncertainty is refined by defining a maximum and minimum for the range of acceptable boundary points for one or more vertices.

At step 908, the uncertainty estimated at each of the plurality of vertices is visualized on the surface model. A level of uncertainty at each vertex may be visually distinguished. For example, different colors may be employed to represent different levels of uncertainty. The levels of uncertainty may be based on the standard deviation (or variance) of the Gaussian distribution.

At step 910, clinical measurements of the target anatomical object are calculated based on the surface model and the uncertainty. The clinical measurements may include a diameter, area, distance, or any other measurement. The clinical measurements may be represented as a range of values or as a mean value plus or minus the standard deviation with a percent confidence interval.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIG. 9. Certain steps of the methods described herein, including one or more of the steps of FIG. 9, may be performed by a server or by another processor in a network-based cloud-computing system. Certain steps of the methods described herein, including one or more of the steps of FIG. 9, may be performed by a client computer in a network-based cloud computing system. The steps of the methods described herein, including one or more of the steps of FIG. 9, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIG. 9, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 10:
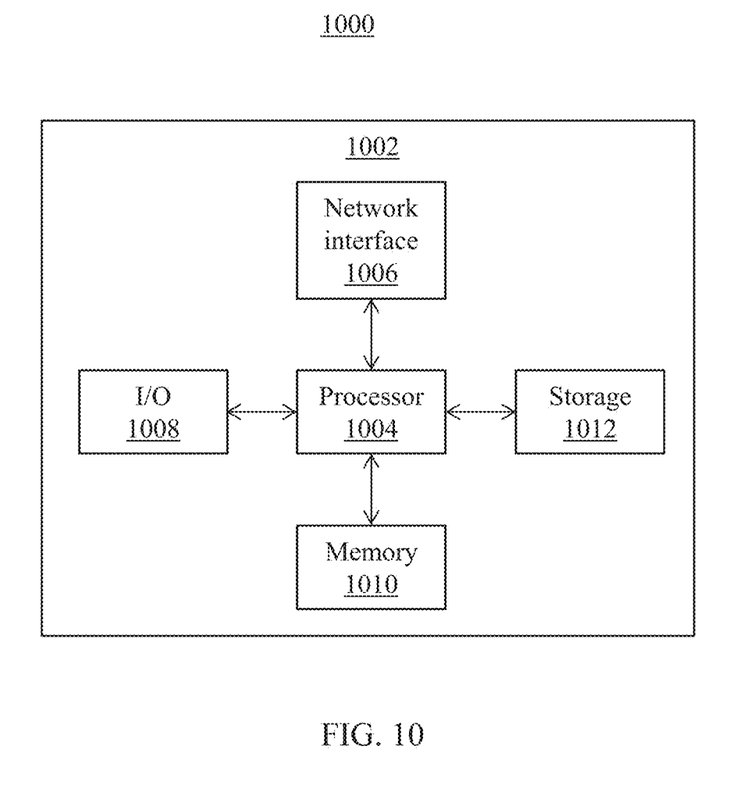
FIG. 10 shows a high-level block diagram of a computer for computing uncertainty in medical imaging data, in accordance with one embodiment.

A high-level block diagram 1000 of an example computer that may be used to implement systems, apparatus, and methods described herein is depicted in FIG. 10. Computer 1002 includes a processor 1004 operatively coupled to a data storage device 1012 and a memory 1010. Processor 1004 controls the overall operation of computer 1002 by executing computer program instructions that define such operations. The computer program instructions may be stored in data storage device 1012, or other computer readable medium, and loaded into memory 1010 when execution of the computer program instructions is desired. Thus, the method steps of FIG. 9 can be defined by the computer program instructions stored in memory 1010 and/or data storage device 1012 and controlled by processor 1004 executing the computer program instructions. For example, the computer program instructions can be implemented as computer executable code programmed by one skilled in the art to perform the method steps of FIGS. 1 and 9 and the modules of FIG. 2. Accordingly, by executing the computer program instructions, the processor 1004 executes the method steps of FIGS. 1 and 9 and modules of FIG. 2. Computer 1002 may also include one or more network interfaces 1006 for communicating with other devices via a network. Computer 1002 may also include one or more input/output devices 1008 that enable user interaction with computer 1002 (e.g., display, keyboard, mouse, speakers, buttons, etc.).

Processor 1004 may include both general and special purpose microprocessors, and may be the sole processor or one of multiple processors of computer 1002. Processor 1004 may include one or more central processing units (CPUs), for example. Processor 1004, data storage device 1012, and/or memory 1010 may include, be supplemented by, or incorporated in, one or more application-specific integrated circuits (ASICs) and/or one or more field programmable gate arrays (FPGAs).

Data storage device 1012 and memory 1010 each include a tangible non-transitory computer readable storage medium. Data storage device 1012, and memory 1010, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1008 may include peripherals, such as a printer, scanner, display screen, etc. For example, input/output devices 1008 may include a display device such as a cathode ray tube (CRT) or liquid crystal display (LCD) monitor for displaying information to the user, a keyboard, and a pointing device such as a mouse or a trackball by which the user can provide input to computer 1002.

Any or all of the systems and apparatus discussed herein, including elements of system 200 of FIG. 2, may be implemented using one or more computers such as computer 1002.

One skilled in the art will recognize that an implementation of an actual computer or computer system may have other structures and may contain other components as well, and that FIG. 10 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for calculating a clinical measurement of a target anatomical object of a patient, comprising:

generating a surface model of a target anatomical object from medical imaging data of a patient;

determining a probability that each of a plurality of points along a surface normal for each of a plurality of vertices of the surface model accurately identifies an image boundary;

estimating uncertainty at each respective vertex of the plurality of vertices of the surface model based on the probabilities determined for the plurality of points along the surface normal for the respective vertex;

visualizing the uncertainty estimated at each of the plurality of vertices on the surface model; and calculating a clinical measurement of the target anatomical object based on the surface model and the uncertainty.

2. The method as recited in claim 1, wherein estimating uncertainty at each respective vertex of the plurality of vertices of the surface model further comprises:

estimating a range of acceptable points from the plurality of points along the surface normal for the respective vertex based on the probabilities determined for the plurality of points along the surface normal for the respective vertex; and fitting a respective uncertainty distribution to the range of acceptable points estimated for each of the plurality of vertices.

3. The method as recited in claim 2, wherein the range of acceptable points corresponds to a probability distribution indicating the probability that each point in the range of acceptable points accurately identifies the image boundary.

4. The method as recited in claim 2, wherein:

determining the probability that each of the plurality of points along the surface normal for each of the plurality of vertices of the surface model accurately identifies the image boundary comprises detecting the probability that each of the plurality of points along the surface normal for each of the plurality of vertices of the surface model accurately identifies the image boundary using a trained classifier; and estimating the range of acceptable points from the plurality of points along the surface normal for the respective vertex comprises estimating the range of acceptable points from the plurality of points along the surface normal for the respective vertex based on a comparison between the probabilities determined for the plurality of points along the surface normal for the respective vertex and a threshold.

5. The method as recited in claim 2, wherein fitting the respective uncertainty distribution to the range of acceptable points estimated for each of the plurality of vertices comprises:

fitting a respective Gaussian distribution to the range of acceptable points estimated for each of the plurality of vertices.

6. The method as recited in claim 5, wherein a mean of the respective Gaussian distribution is at the vertex and a standard deviation defines a confidence interval for the vertex.

7. The method as recited in claim 2, further comprising:

refining the uncertainty by defining a minimum and a maximum for the range of acceptable points for at least one of the plurality of vertices.

8. The method as recited in claim 1, wherein generating the surface model of the target anatomical object further comprises:

segmenting the target anatomical object using marginal space learning based segmentation.

9. The method as recited in claim 8, wherein segmenting the target anatomical object using marginal space learning based segmentation further comprises:

detecting a bounding box encapsulating the target anatomical object in the medical imaging data using marginal space learning;

detecting anatomical landmarks of the target anatomical object within the bounding box; and fitting a surface model of the target anatomical object to the detected anatomical landmarks.

10. The method as recited in claim 1, wherein visualizing the uncertainty estimated at each of the plurality of vertices on the surface model further comprises:

displaying a visualization of the surface model with a color representing a level of uncertainty for each of the plurality of vertices, wherein the level of uncertainty for each of the plurality of vertices is based on a standard deviation of a respective uncertainty distribution estimated for each of the plurality of vertices.

11. The method as recited in claim 1, wherein calculating the clinical measurement of the target anatomical object based on the surface model and the uncertainty comprises at least one of:

calculating a range of the clinical measurement based on the surface model and the uncertainty; and calculating a mean value and a standard deviation value for the clinical measurement with an associated confidence interval based on the surface model and the uncertainty.

12. An apparatus for calculating a clinical measurement of a target anatomical object of a patient, comprising:

means for generating a surface model of a target anatomical object from medical imaging data of a patient;

means for determining a probability that each of a plurality of points along a surface normal for each of a plurality of vertices of the surface model accurately identifies an image boundary;

means for estimating uncertainty at each respective vertex of the plurality of vertices of the surface model based on the probabilities determined for the plurality of points along the surface normal for the respective vertex;

means for visualizing the uncertainty estimated at each of the plurality of vertices on the surface model; and means for calculating a clinical measurement of the target anatomical object based on the surface model and the uncertainty.

13. The apparatus as recited in claim 12, wherein the means for estimating uncertainty at each respective vertex of the plurality of vertices of the surface model further comprises:

means for estimating a range of acceptable points from the plurality of points along the surface normal for the respective vertex based on the probabilities for the plurality of points along the surface normal for the respective vertex; and means for fitting a respective uncertainty distribution to the range of acceptable points estimated for each of the plurality of vertices.

14. The apparatus as recited in claim 13, wherein the range of acceptable points corresponds to a probability distribution indicating the probability that each point in the range of acceptable points accurately identifies the image boundary.

15. The apparatus as recited in claim 13, wherein:

the means for determining the probability that each of the plurality of points along the surface normal for each of the plurality of vertices of the surface model accurately identifies the image boundary comprises means for detecting the probability that each of the plurality of points along the surface normal for each of the plurality of vertices of the surface model accurately identifies the image boundary using a trained classifier; and the means for estimating the range of acceptable points from the plurality of points along the surface normal for the respective vertex comprises means for estimating the range of acceptable points from the plurality of points along the surface normal for the respective vertex based on a comparison between the probabilities determined for the plurality of points along the surface normal for the respective vertex and a threshold.

16. The apparatus as recited in claim 13, wherein the means for fitting the respective uncertainty distribution to the range of acceptable points estimated for each of the plurality of vertices comprises:

means for fitting a respective Gaussian distribution to the range of acceptable points estimated for each of the plurality of vertices.

17. The apparatus as recited in claim 13, further comprising:

means tor refining the uncertainty by defining a minimum and a maximum for the range of acceptable points for at least one of the plurality of vertices.

18. The apparatus as recited in claim 12, wherein the means for generating the surface model of the target anatomical object further comprises:

means for segmenting the target anatomical object using marginal space learning based segmentation.

19. The apparatus as recited in claim 18, wherein the means for segmenting the target anatomical object using marginal space learning based segmentation further comprises:

means for detecting a bounding box encapsulating the target anatomical object in the medical imaging data using marginal space learning;

means for detecting anatomical landmarks of the target anatomical object within the bounding box; and means for fitting a surface model of the target anatomical object to the detected anatomical landmarks.

20. The apparatus as recited in claim 12, wherein the means for visualizing the uncertainty estimated at each of the plurality of vertices on the surface model further comprises:

means for displaying a visualization of the surface model with a color representing a level of uncertainty for each of the plurality of vertices, wherein the level of uncertainty for each of the plurality of vertices is based on a standard deviation of a respective uncertainty distribution estimated for each of the plurality of vertices.

21. The apparatus as recited in claim 12, wherein the means for calculating the clinical measurement of the target anatomical object based on the surface model and the uncertainty comprises at least one of:

means for calculating a range of the clinical measurement based on the surface model and the uncertainty; and means for calculating a mean value and a standard deviation value for the clinical measurement with an associated confidence interval based on the surface model and the uncertainty.

22. A non-transitory computer readable medium storing computer program instructions for calculating a clinical measurement of a target anatomical object of a patient, the computer program instructions when executed by a processor cause the processor to perform operations comprising:

generating a surface model of a target anatomical object from medical imaging data of a patient;

determining a probability that each of a plurality of points along a surface normal for each of a plurality of vertices of the surface model accurately identifies an image boundary;

estimating uncertainty at each respective vertex of the plurality of vertices of the surface model based on the probabilities determined for the plurality of points along the surface normal for the respective vertex;

visualizing the uncertainty estimated at each of the plurality of vertices on the surface model; and calculating a clinical measurement of the target anatomical object based on the surface model and the uncertainty.

23. The non-transitory computer readable medium as recited in claim 22, wherein estimating uncertainty at each respective vertex of the plurality of vertices of the surface model further comprises:

estimating a range of acceptable points from the plurality of points along the surface normal for the respective vertex based on the probabilities determined for the plurality of points along the surface normal for the respective vertex; and fitting a respective uncertainty distribution to the range of acceptable points estimated for each of the plurality of vertices.

24. The non-transitory computer readable medium as recited in claim 23, wherein the range of acceptable points corresponds to a probability distribution indicating the probability that each point in the range of acceptable points accurately identifies the image boundary.

25. The non-transitory computer readable medium as recited in claim 23, the operations further comprising:

refining the uncertainty by defining a minimum and a maximum for the range of acceptable points for at least one of the plurality of vertices.

26. The non-transitory computer readable medium as recited in claim 22, wherein generating the surface model of the target anatomical object further comprises:

segmenting the target anatomical object using marginal space learning based segmentation.

27. The non-transitory computer readable medium as recited in claim 26, wherein segmenting the target anatomical object using marginal space learning based segmentation further comprises:

detecting a bounding box encapsulating the target anatomical object in the medical imaging data using marginal space learning;

detecting anatomical landmarks of the target anatomical object within the bounding box; and fitting a surface model of the target anatomical object to the detected anatomical landmarks.

28. The non-transitory computer readable medium as recited in claim 22, wherein visualizing the uncertainty estimated at each of the plurality of vertices on the surface model further comprises:

displaying a visualization of the surface model with a color representing a level of uncertainty for each of the plurality of vertices, wherein the level of uncertainty for each of the plurality of vertices is based on a standard deviation of a respective uncertainty distribution estimated for each of the plurality of vertices.

29. The method as recited in claim 22, wherein calculating the clinical measurement of the target anatomical object based on the surface model and the uncertainty comprises at least one of:

calculating a range of the clinical measurement based on the surface model and the uncertainty; and calculating a mean value and a standard deviation value for the clinical measurement with an associated confidence interval based on the surface model and the uncertainty.

* * * * *